US008554064B1

(12) United States Patent
Dinh et al.

(10) Patent No.: US 8,554,064 B1
(45) Date of Patent: Oct. 8, 2013

(54) METHOD AND APPARATUS FOR GENERATING VAPOR AT HIGH RATES

(75) Inventors: Thuc Dinh, Shakopee, MN (US); Yamin Ma, Roseville, MN (US); Benjamin Y. H. Liu, North Oaks, MN (US)

(73) Assignee: MSP Corporation, Shoreview, MN (US)

( * ) Notice: Subject to any disclaimer, the term of this patent is extended or adjusted under 35 U.S.C. 154(b) by 0 days.

(21) Appl. No.: 13/333,373

(22) Filed: Dec. 21, 2011

Related U.S. Application Data

(60) Provisional application No. 61/427,299, filed on Dec. 27, 2010.

(51) Int. Cl.
| | |
|---|---|
| *F22B 29/06* | (2006.01) |
| *F22B 1/28* | (2006.01) |
| *A01G 13/06* | (2006.01) |
| *A61M 16/00* | (2006.01) |
| *A61H 33/06* | (2006.01) |
| *B01D 3/06* | (2006.01) |
| *A47J 27/00* | (2006.01) |
| *A47J 31/00* | (2006.01) |
| *F24H 1/18* | (2006.01) |
| *F24H 1/10* | (2006.01) |
| *B05B 1/24* | (2006.01) |

(52) U.S. Cl.
USPC ............ 392/397; 392/386; 392/391; 392/392; 392/394; 392/396; 392/399; 392/480; 392/484

(58) Field of Classification Search
USPC .................. 392/394, 396–398, 465, 468, 469, 392/478, 479, 496, 386, 391–392, 399–400, 392/441, 458, 459, 473, 480, 482, 484
See application file for complete search history.

(56) References Cited

U.S. PATENT DOCUMENTS

| | | | | |
|---|---|---|---|---|
| 1,409,019 | A * | 3/1922 | Parnell-Smith | 392/489 |
| 1,941,548 | A * | 1/1934 | Friedheim | 172/17 |
| 2,055,949 | A * | 9/1936 | Sharp | 122/33 |
| 3,119,004 | A * | 1/1964 | Hoop | 392/399 |
| 3,174,326 | A * | 3/1965 | Carle et al. | 73/23.35 |
| 3,507,627 | A * | 4/1970 | Frant et al. | 422/654 |
| 3,530,930 | A * | 9/1970 | Oldfield | 165/133 |
| 4,439,669 | A * | 3/1984 | Ryffel | 392/320 |
| 6,339,678 | B1 * | 1/2002 | Sorensen | 392/386 |
| 7,167,776 | B2 * | 1/2007 | Maharajh et al. | 700/266 |
| 7,203,419 | B2 * | 4/2007 | Malone et al. | 392/468 |
| 7,404,862 | B2 * | 7/2008 | Shtein et al. | 118/726 |
| 2008/0273868 | A1 * | 11/2008 | Boussemart et al. | 392/479 |

* cited by examiner

*Primary Examiner* — Joseph M Pelham
*Assistant Examiner* — Gyounghyun Bae
(74) *Attorney, Agent, or Firm* — Westman, Champlin & Kelly, PA; Z. Peter Sawicki

(57) ABSTRACT

The present disclosure relates to an apparatus and a method for vaporizing a liquid to form vapor preferably in a gas stream. The apparatus includes a composite metal structure, the structure comprising a plurality of passageways for providing heat to vaporize the liquid in the gas stream to form a gas/vapor mixture. A non-corrosive interface lies between the metal structure and the gas/vapor mixture, the interface being chemically inert to the gas/vapor mixture and the structure permitting heat to be conducted rapidly therethrough to vaporize the liquid. The apparatus further includes an inlet for the gas and an inlet for the liquid to be vaporized to flow into the plurality of passageways and an exit through which the gas/vapor mixture exits the apparatus.

12 Claims, 4 Drawing Sheets

METHOD AND APPARATUS FOR GENERATING VAPOR AT HIGH RATES

CROSS-REFERENCE TO RELATED APPLICATION

The present application is based on and claims the benefit of U.S. provisional patent application Ser. No. 61/427,299, filed Dec. 27, 2010, the content of which is hereby incorporated by reference in its entirety.

BACKGROUND OF THE DISCLOSURE

The process of creating a vapor from a liquid usually involves heating the liquid to a sufficiently high temperature to form vapor. To generate vapor at a high rate, it is necessary to supply a substantial amount of energy in a short time to the liquid so that the needed vaporization energy can be provided. Traditionally, the output of a vapor generation apparatus can be increased by increasing the operating temperature to allow more heat to flow into the liquid to form vapor. Alternatively, a larger heat transfer surface area can be provided to increase the vapor generation rate. Both approaches have been used in the past and are well known to those skilled in the art of industrial equipment design. Equipment such as industrial boilers—for generating steam from water—and refrigerant evaporator coil—for evaporating a liquid refrigerant to form vapor for cooling, refrigeration or air conditioning purposes—are examples where such approaches are used.

In semiconductor applications, a wide variety of precursor chemicals are available in liquid form to create vapor for thin film deposition on a substrate by a vapor phase process in semiconductor, integrated circuit device manufacturing. Processes such as chemical vapor deposition (CVD), plasma-enhanced chemical vapor deposition (PECVDP), metal-organic CVD (MOCVD), atmosphere pressure chemical vapor deposition (APCVD) and atomic layer deposition (ALD) are well known to those skilled in the art of semiconductor device fabrication. Some precursor chemicals such as metal-organic compounds can decompose at high temperatures to form undesirable by-products to cause process or equipment contamination. For such applications, the heating temperature must be kept low to avoid thermal decomposition and by-product formation. Increasing the heat transfer surface area will generally cause the overall physical size of the apparatus to increase, thus making the device less responsive to changing vapor demands in the process. The response speed of the apparatus will thus decrease. As a result, the traditional approach to increasing vaporization rate is not suitable for all applications.

SUMMARY OF THE DISCLOSURE

An apparatus described herein is used to vaporize a liquid to form a vapor. The apparatus includes a composite metal structure, the structure comprising two metals forming a layered composite metal structure, the metals having different thermal conductivities, one metal having a low thermal conductivity and the other metal having a high thermal conductivity, the metal with the low thermal conductivity being in direct physical contact with the vapor, the metal with the high thermal conductivity not being in direct physical contact with the vapor thereby allowing heat from the source to conduct rapidly throughout the structure, the structure being provided with an inlet for the liquid to enter, and a multitude of flow passageways positioned within the metal structure for the liquid to form the vapor. The apparatus also includes an outlet for the vapor to flow out of the apparatus.

The disclosure also includes a method to vaporize a liquid. The method includes introducing into an apparatus the liquid, through an inlet to generate a vapor. The apparatus includes a composite metal structure, and a source of heat in contact with the structure. The structure comprises two metals having different thermal conductivities. The thermal conductivity of one metal is low while the thermal conductivity of the other metal is high. The metals form a composite metal structure wherein the metal with the low thermal conductivity is in direct physical contact with the vapor, and the metal with the high thermal conductivity is not in direct physical contact with the vapor, thus allowing heat to conduct rapidly throughout the structure due to the composition of the structure. The method also includes vaporizing the liquid to form the vapor while flowing through a multitude of flow passageways within the structure, the flow passageways being defined by the composite structure, and exiting the vapor through an outlet to flow out of the apparatus.

This disclosure also includes an apparatus for vaporizing liquids to form a vapor in a gas stream. The apparatus includes a structure that comprises a plurality of passageways for providing heat to vaporize the liquid in the gas stream, the passageways being disposed within a metal having a thermal conductivity of at least 5 times higher than that of stainless steel. A non-corrosive layer is disposed between the metal and the vaporizing liquid, the non-corrosive layer being chemically inert to the liquid being vaporized and the gas. The metal permits heat to be conducted rapidly throughout the structure to the liquid for vaporizing the liquid to form a gas/vapor mixture. The apparatus further comprises inlets for the gas and the liquid to flow into the plurality of passageways and an exit through which the gas/vapor mixture exits the apparatus.

DESCRIPTION OF THE EXEMPLARY EMBODIMENTS

The present disclosure describes an approach to raising the vapor output and the capacity of a vapor generating apparatus without increasing its operating temperature or its physical size or both. The approach is particularly desirable for semiconductor device fabrication where a small compact device capable of generating vapor at a high rate is particularly advantageous.

For semiconductor device fabrication the precursor vapor generated by the vaporization apparatus must be pure and substantially free of particulate and gaseous contaminants. Material that can come into direct physical contact with the gas, vapor, and liquid flowing through the apparatus are referred to as "wetted surface." Traditionally stainless steel is used because stainless steel can provide a clean and corrosion-resistant surface needed for the application.

While stainless steel is desirable from the point of view of vapor purity, its heat conducting or heat transfer properties are not particularly desirable or advantageous. The present disclosure describes an approach where stainless steel is used in combination with another metal in a vapor generating apparatus in a manner so as to provide both a clean, contaminant free surface and the high vaporization rate needed for the application.

While the invention of the present disclosure is particularly advantageous for generating vapor from liquid organo-metallic precursors, its use is not limited to such precursors only. In semiconductor device fabrication substances such as water and isopropyl alcohol (IPA) are often used. Water in vapor form can be used in a vapor phase deposition process to provide a source of oxygen needed for deposition and IPA vapor is useful for wafer drying following wet cleaning. Generating high purity water and IPA vapor from liquid water and IPA is, therefore, also important for semiconductor device fabrication.

While the present invention is directed towards applications in the semiconductor industry, it is also suitable for other applications in other industries where similar requirements exist for vapor generation at a high rate. Examples include fabricating photovoltaic solar cells for power generation and applying anti-reflective coatings on glass to improve the efficiency of solar cells. These applications generally require very high vapor generation rates, because very large surface areas are needed for solar power generation. The invention of this disclosure is also advantageous for these applications.

Figure 1:
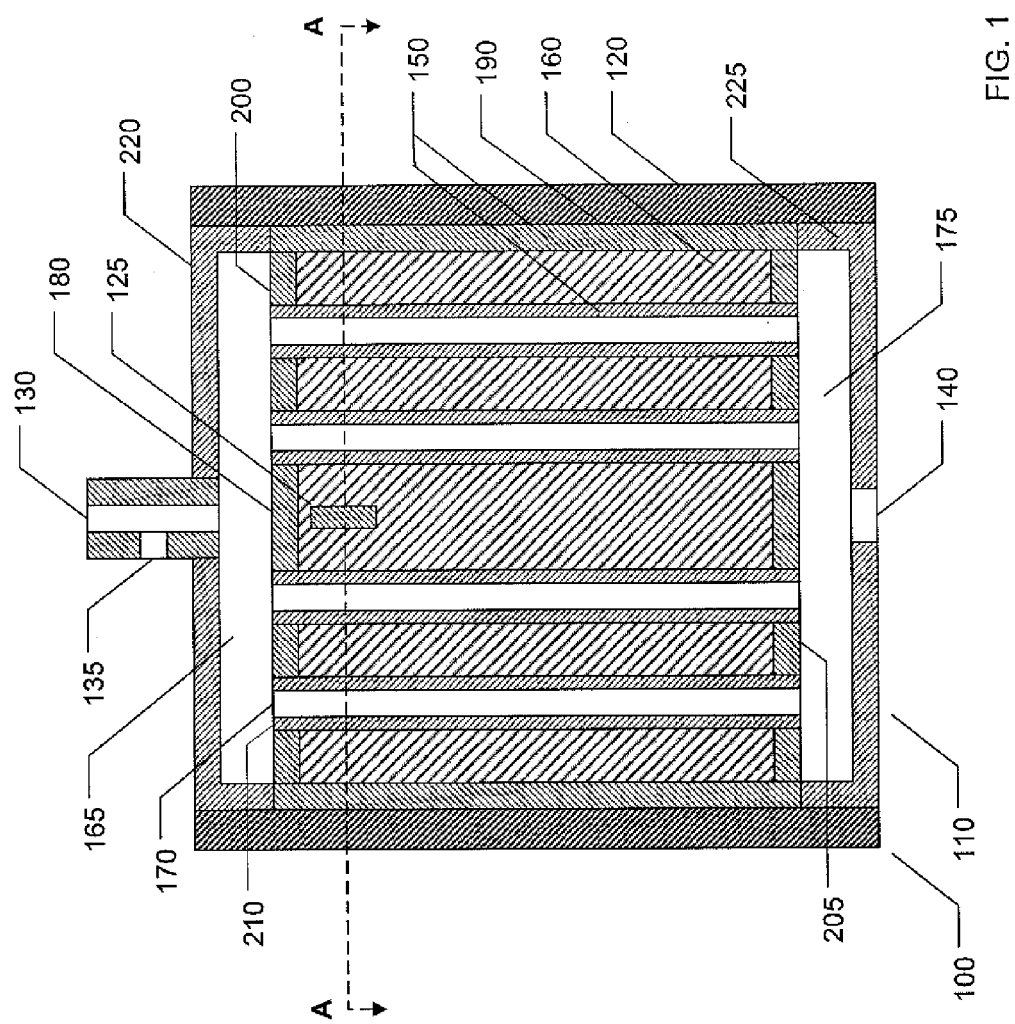
FIG. 1 is a vertical sectional view of the schematic vapor generating apparatus in its preferred embodiment
Figure 2:
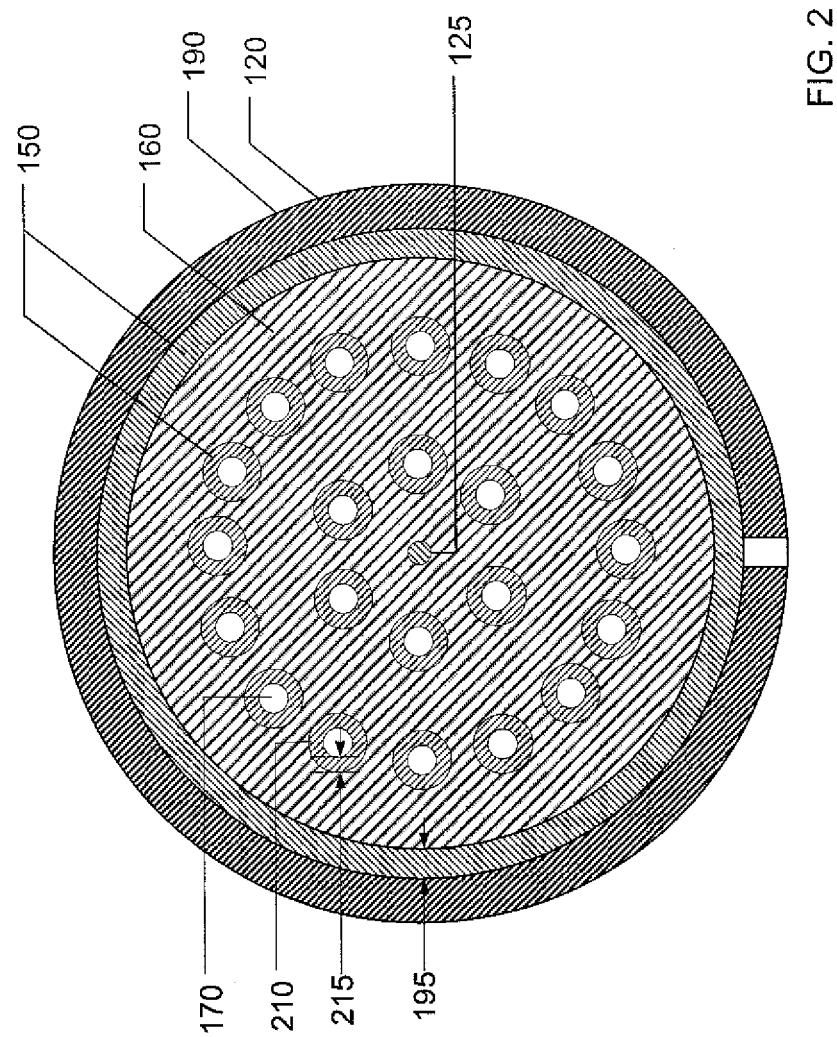
FIG. 2 is a horizontal sectional view along line A-A of the schematic vapor generating apparatus in its preferred embodiment shown in FIG. 1

FIG. 1 is a vertical sectional view of the vapor generating apparatus shown in its one embodiment and FIG. 2 is the horizontal sectional view of the same apparatus along line A-A of FIG. 1. Like reference characters will be used for like elements throughout the figures.

The vapor generating apparatus, which is referred to as a vaporizer, is generally indicated at 100. The apparatus includes a composite metal structure 110, a heater 120 in good thermal contact with the structure and a temperature sensor 125 also in good thermal contact with the structure. By composite is meant two dissimilar metals in adjoining heat-conducting contact, such as at least one of the metals being a layer in heat conducting contact with the other metal. Preferably, the heat-conducting contact between the two dissimilar metals is continuous. Heater 120 is generally an electric heater, connected to a source of electric power, which is not shown, through a temperature controller, also not shown. The electrical power input to heater 120 is controlled by the controller so that the composite metal structure 110 can be controlled to a specific set-point temperature based on the electrical signal generated by temperature sensor 125.

The composite metal structure 110 has an inlet 130 for a carrier gas to enter and an inlet 135 for a liquid to enter. Upon entering the heated metal structure the gas and liquid encounter the heated metal surfaces in the structure causing the gas to become heated and the liquid to be vaporized to form a gas/vapor mixture. The mixture then flows out of the composite metal structure through outlet 140 on the structure. Further, the gas and liquid inlets 130 and 135 can be juxtapositioned to enable gas entering the structure through inlet 130 to atomize liquid entering the structure through inlet 135 to form a droplet spray to facilitate the vaporization of the liquid in droplet form.

Conventional vapor generating apparatus is usually constructed of a single material, typically stainless steel, which is chosen for its property of being able to form a clean, contaminant-free surface that is also corrosion resistant. The composite metal structure 110 of the present disclosure is fabricated from two different metals, Metal-A 150 is chosen for its clean and corrosion-resistant surface properties, and metal-B 160, for its favorable heat conducting properties. These two metals form a composite metal structure for fabricating the vapor generating apparatus described herein.

As the gas and liquid enter the structure through the respective gas and liquid inlets, 130 and 135, they flow into an inlet plenum, 165, then through a plurality of parallel flow passageways, 170, into an exit plenum 175. Heat added to the gas and liquid during their passage through the heated composite metal structure causes the gas to become heated and the liquid to be heated and vaporized. The resulting gas/vapor mixture then flows out of the composite metal structure through outlet 140.

In one embodiment, Metal-A 150 is stainless steel, typically number 316 stainless steel, and metal-B 160 is a metal with a higher thermal conductivity or thermal diffusivity than Metal-A. Typically metal-B is aluminum or copper depending on the application. The vaporization apparatus is designed so that all interior surfaces that are exposed to the gas, liquid or vapor, including the gas and liquid inlet, 130 and 135, the inlet and outlet plenums, 165 and 175, and the parallel flow passageways, 170 are stainless steel with metal-B 160, which is aluminum or copper, being separated from gas, liquid and vapor by solid, impermeable walls of stainless steel. Metal-A and metal-B are in continuous heat conducting contact throughout metal-A's area of contact with the gas, liquid and vapor.

As mentioned earlier, metal-A is chosen for its contaminant-free, corrosion resistant properties, so that the gas, liquid and vapor flowing through the apparatus will come in direct physical contact only with metal-A and not become contaminated as a result of the direct physical contact with metal-A. Metal-B is chosen for its favorable heat transfer properties, so that heat generated by electric heater 120 can be conducted easily and quickly to the stainless steel surfaces for vaporization purposes.

The rate of heat transfer through a heat conducting path with a cross-sectional area A and length L is proportional to the area and inversely proportional to the length, i.e.

$$Q = \frac{kA\Delta T}{L} = K\Delta T = \frac{\Delta T}{R}$$

where Q is the heat transfer rate, ΔT is the temperature drop from one end of the path to the other end, and k is the thermal conductivity of the material. In the above equation the symbols, K and R, are defined as the total thermal conductance and the total resistance of the conducting path. At a specific temperature difference, ΔT, along a specific conducting path the heat transfer rate, Q, the total thermal conductance, K, will be proportional to the thermal conductivity, k, of the material. The total thermal resistance, R of the path will be inversely proportional to the thermal conductivity, k.

A solid, such as a metal, with a non-uniform temperature at one instant, will see the stored heat in the solid diffuse from a region of high temperature to regions of lower temperature. The rate of thermal diffusion is governed by the parameter, $$\alpha = \frac{k}{\rho C_p}$$

where $$\alpha = \frac{k}{\rho C_p}$$

is the thermal diffusivity, $\rho$ is the density, and $C_p$ is the specific heat at constant pressure. The higher the thermal diffusivity, $\alpha$, the higher is the rate of heat diffusion through the solid to cause its temperature to become uniform more quickly.

The vaporization apparatus of FIG. 1 is generally operated at a specific set-point temperature as indicated by temperature sensor 125. During standby and with gas flowing through inlet 130 into the composite metal structure 110 only, electric heater 120 will provide the needed power input to the structure to heat the composite structure 110 to an elevated temperature above the ambient, thereby causing the gas to be heated as it flows through the structure. Since gas has a low density, the power needed to heat the gas will be relatively small. When liquid begins to flow through inlet 135 into the composite metal structure and impinges on the hot metal surface 180 directly below the liquid inlet and begins to vaporize, it will extract considerable amount of heat from the underlying hot metal below surface 180 causing the temperature of the metal to drop. The temperature sensor 125, which is located below surface 180, will sense this temperature drop quickly, thereby signaling the controller to provide more electrical power to the electric heater 120 in order to cause more heat to flow into the composite metal structure 110 and to restore the cold metal below surface 180 to the set point value. Because Metal-B has a high thermal conductivity, more heat can conduct through Metal-B to meet the vaporization energy needed to vaporize the cold liquid entering through liquid inlet 135 to form vapor. The vaporization capacity of the vaporizer can thus be increased because more heat can conduct through metal-B from the electric heater 120 to the cold temperature region where heat is needed the most for liquid vaporization.

Table 1 shows some typical values for the thermal conductivity and thermal diffusivity of several metals. These are listed in columns 2 and 4. In columns 3 and 5 the ratio of the thermal conductivity and diffusivity to those of stainless steel are listed. Among the metals listed, silver and gold have the highest thermal conductivity and highest thermal diffusivity with thermal conductivity being 25.6 and 19.3 times, and thermal diffusivity being 39.4 and 30.2 times of those of stainless steel. Copper and aluminum have lower thermal conductivity and diffusivity compared to silver and gold, but their thermal conductivity and thermal diffusivity are still respectively 23 and 13 times and 26.7 and 20.0 times those of stainless steel. Silver and gold, because of their high cost can be used in special circumstances, but copper and aluminum, which are much lower in cost, are generally preferred for most applications, where the thermal conductivity and thermal diffusivity of the lower cost copper and aluminum are adequate. If stainless steel is used in contact with the gas/vapor mixture, metal-B should have a thermal conductivity and thermal diffusivity significantly higher than stainless steel. Metal-B can be a pure metal like copper or aluminum or a metal alloy with a preferred thermal conductivity at least 5 times that of the stainless steel.

TABLE 1

Typical Thermal Conductivity and Thermal Diffusivity of Metals

| Metal | Thermal Conductivity | | Thermal Diffusivity | |
|---|---|---|---|---|
| | (W·m⁻¹K⁻¹) | Ratio to SS | (10⁻⁶ m²/s) | Ratio to SS |
| Silver | 418 | 25.6 | 165.63 | 39.4 |
| Gold | 315 | 19.3 | 127 | 30.2 |
| Copper | 385 | 23 | 112.34 | 26.7 |
| Aluminum | 220 | 13 | 84.18 | 20.0 |
| Stainless Steel (304A SS) | 16.3 | 1.0 | 4.2 | 1.0 |

The vaporization apparatus of FIG. 1 and FIG. 2 has a vacuum tight and leak-free design, which is needed in semiconductor thin film deposition applications involving vacuum deposition processes. In this design, the three separate stainless steel pieces, the tubular shaped body, 190, with a thickness 195, the upper end cap, 220 and lower end cap, 225 are welded together to form a leak-free envelop. A multitude of stainless metal tubes, 210, are welded to the two circular end plates, 200 and 205 to form the multitude of flow passageways, 170, to allow the gas, liquid and vapor to flow through and be heated and vaporized. The stainless metal tubes, 210, are in good thermal contact with metal-B, 160, and their wall thickness 215 are quite thin to allow heat from Metal-B to conduct through the thin stainless steel walls to the gas, liquid, and vapor flowing through the tubes. Metal-B is a circular block of metal drilled to accommodate the stainless tubes, metal-B being copper, aluminum, another metal or a metal alloy having a thermal conductivity at least five times that of stainless steel.

Figure 3:
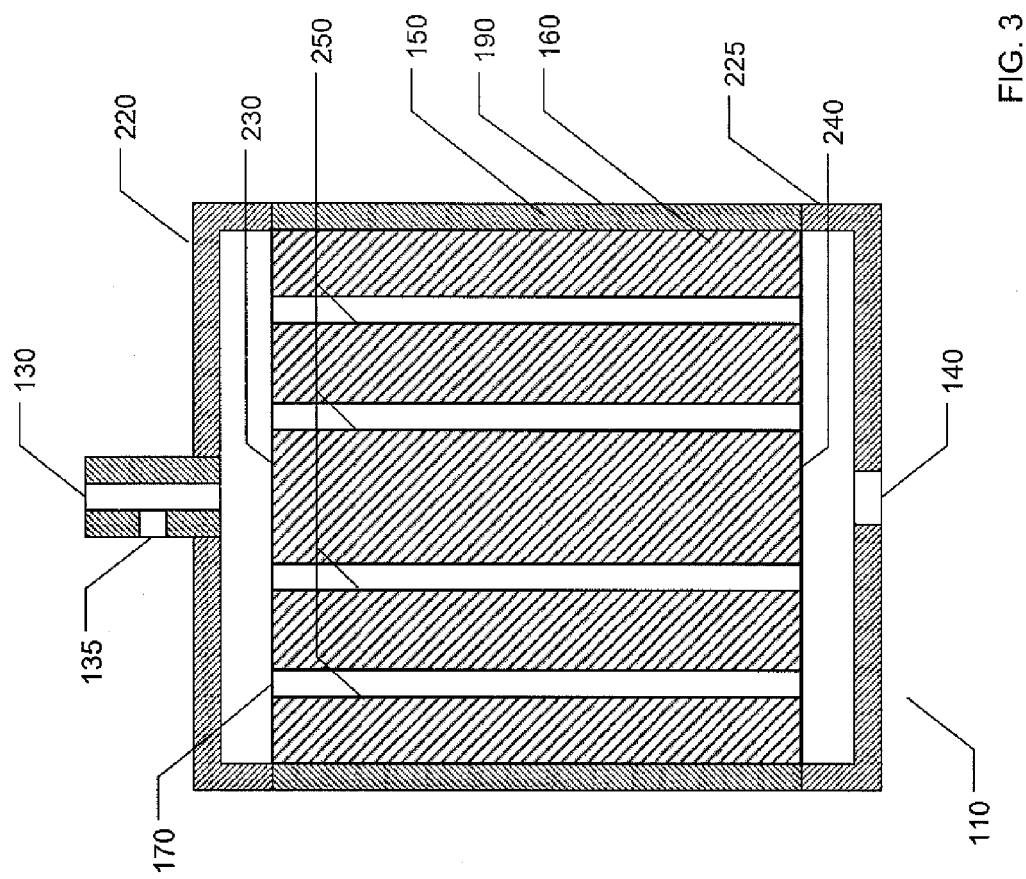
FIG. 3 is a vertical sectional view of an alternate composite metal structure for vapor generation

FIG. 3 is a vertical sectional view of an alternate design of the composite metal structure. In this design, the composite metal structure is shown generally at 110. The outer envelope of the structure, formed by welding the vertical tube body 190 and the upper and lower end caps, 220 and 225, is made of Metal-A 150, which is typically stainless steel. The metal piece 160 is made of Metal-B, which is typically copper or aluminum. Metal piece 160 carries a multitude of holes 170 to provide flow passageways for the gas, liquid and vapor to flow through to allow the liquid to be vaporized and the gas and vapor to be heated. Metal piece 160 is treated with an inert surface coating so that its upper and lower surfaces, 230 and 240, as well as the inside wall surfaces 250 of the flow passageways are covered with a contaminant free and corrosion resistant surface coating. Suitable coating material includes, but is not limited, to silicon oxide, SiO2, silicon nitride, Si3N4, and titanium nitride, TiN. Many of the inert surface coatings can be created by the same semiconductor deposition processes for which the vaporization apparatus is intended in its application. Contaminant free and corrosion resistant coatings as thin as 1.0 µm or thinner can be used.

In comparison to the metal composite structure of FIG. 1, the stainless steel tubes 210 are typically not less than 0.010" equivalent to approximately 250 µm, for a quarter 1/4" diameter stainless steel tube. Since the thermal conductance, K, of a conducting layer is proportional to the thermal conductivity, K, of the material and inversely proportional to its thickness, L, according the equation $$Q = \frac{kA\Delta T}{L} = K\Delta T = \frac{\Delta T}{R},$$

a 1 μm thick layer of SiO2 layer in the form a quartz with a thermal conductivity of 1.3 Wm$^{-1}$K will have a thermal conductance that is $(250/1)(1.3/16.3)=19.9 \approx 20$ times higher than that a 250 μm thick layer of stainless steel with a thermal conductivity of 16.3 Wm$^{-1}$K As a result, the conductance for heat transfer in comparison with the design of FIG. 1 and FIG. 2.

Figure 4:
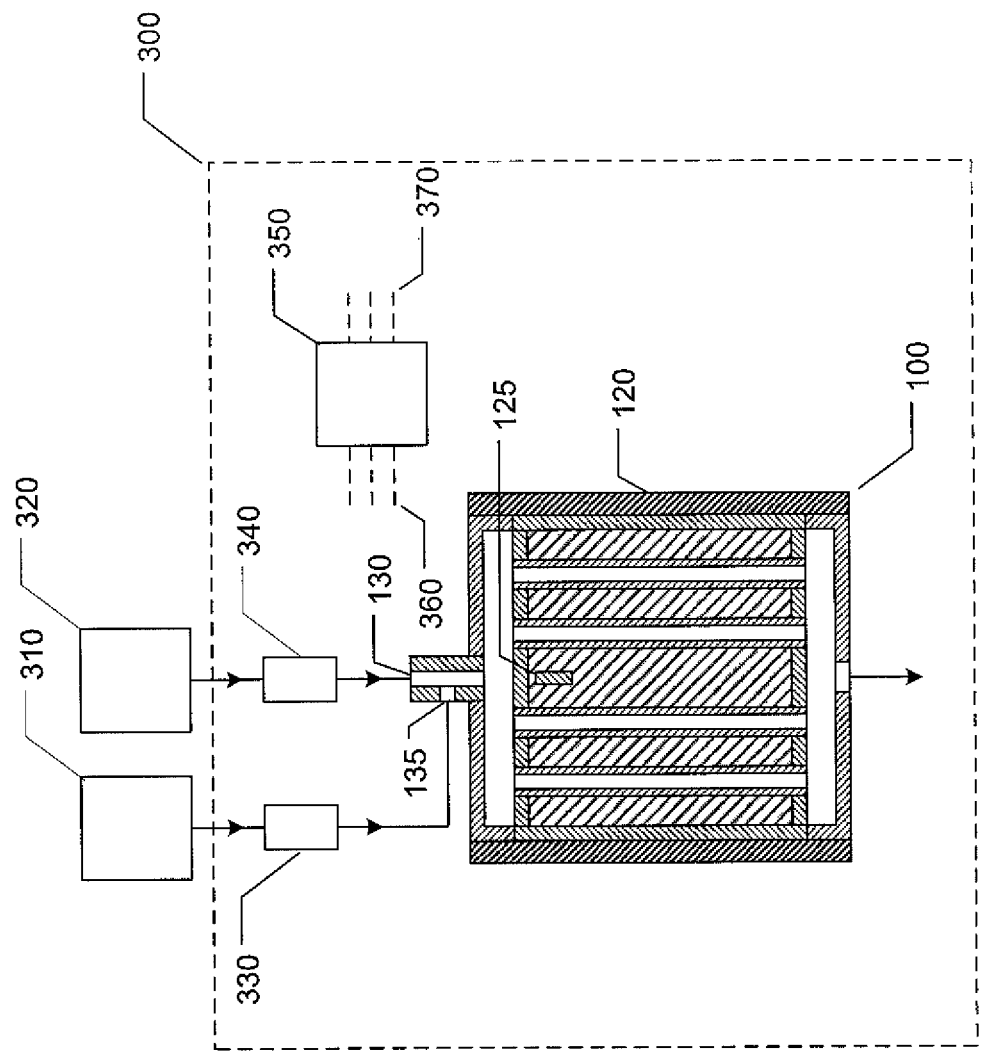
FIG. 4 is a schematic diagram of a vapor generation system of the present disclosure

FIG. 4 shows a vapor generating system making use of the composite metal structures of the present disclosure. The system is shown generally at 300 and connected to a source of liquid 310 and a source of gas 320. Connected to these sources are a liquid flow controller 330 and a gas flow controller 340 in order to provide controlled rates of liquid and gas flow into the respective liquid and gas inlets, 135 and 130, in the vaporization apparatus. The system also includes a vaporization system controller 350, which is provided with a multitude of input lines 360 to receive the output signal from temperature sensor 125 and liquid and gas flow sensors in the liquid and gas flow controllers 330 and 340. Controller 350 also provides the proper control signal through output lines 370 in order to control the power input to the electric heater and the set-point electrical signal for the flow controllers in order to control the temperature of the vaporization apparatus and the liquid and gas flow rates to their respective set-point values.

Although the present invention has been described with reference to preferred embodiments, workers skilled in the art will recognize that changes may be made in form and detail without departing from the spirit and scope of the invention.

What is claimed is:

1. An apparatus for vaporizing a liquid to form vapor, said apparatus comprising a composite metal structure, said structure comprising two metals having different thermal conductivities, one metal having a lower thermal conductivity and one metal having a higher thermal conductivity, said metal with the lower thermal conductivity being in physical contact with said vapor, said metal with the higher thermal conductivity not being in direct physical contact with said vapor, to allow heat from a source to conduct throughout said structure, said structure being provided with an inlet for the liquid to enter, and a multitude of flow passageways in said metal with a high thermal conductivity for said liquid to flow through and be heated and vaporized to form the vapor, and an outlet for the vapor to flow out of said structure.

2. The apparatus of claim 1 said metal with the higher thermal conductivity being separated from said liquid and vapor by said metal with the lower thermal conductivity.

3. The apparatus of claim 1 said metal with the higher thermal conductivity being separated from said liquid and vapor by an inert layer of non-contaminating and corrosion-resistant surface coating material.

4. The apparatus of claim 3, said inert layer of non-contaminating and corrosion resistant surface coating material being silicon dioxide, silicon nitride, or titanium nitride.

5. The apparatus of claim 1 said metal having the lower thermal conductivity comprising stainless steel.

6. The apparatus of claim 1 said metal having the higher thermal conductivity comprising gold, silver, copper, silver, or aluminum or a metal or metal alloy with a thermal conductivity at least five times that of stainless steel.

7. The apparatus of claim 1, said source comprising an electric heater.

8. The apparatus of claim 1 including a liquid flow controller to control the rate of liquid flow into said apparatus.

9. The apparatus of claim 1 and further comprising an inlet for a carrier gas to enter into the apparatus and to mix with the liquid to form a gas/vapor mixture.

10. The apparatus of claim 9 including a gas flow controller to control the rate of gas flow into said apparatus.

11. The apparatus of claim 1 including a temperature sensor and a temperature controller to control the temperature of said apparatus to a desired value.

12. The apparatus of claim 9 in which the gas and liquid entering through the respective inlets are in juxtaposition to allow said gas to atomize said liquid to form droplets for vaporization.

* * * * *

UNITED STATES PATENT AND TRADEMARK OFFICE
CERTIFICATE OF CORRECTION

Page 1 of 1

PATENT NO. : 8,554,064 B1
APPLICATION NO. : 13/333373
DATED : October 8, 2013
INVENTOR(S) : Thuc Dinh, Yamin Ma and Benjamin Y. H. Liu It is certified that error appears in the above-identified patent and that said Letters Patent is hereby corrected as shown below:

In the Claims:

Claim 6, Column 8, Line 19, the second instance of "silver" should be deleted

Signed and Sealed this
Nineteenth Day of August, 2014

Michelle K. Lee
*Deputy Director of the United States Patent and Trademark Office*